United States Patent
Cho et al.

(10) Patent No.: US 9,027,182 B2
(45) Date of Patent: May 12, 2015

(54) FUNCTIONAL TABLE FOR TRANSFERRING PATIENT

(75) Inventors: Moo Seong Cho, Gyeongsan-si (KR); Jae Young Bae, Daegu-si (KR)

(73) Assignee: Keimyung University Industry Academic Cooperation Foundation, Daegu-Si (KR)

( * ) Notice: Subject to any disclaimer, the term of this patent is extended or adjusted under 35 U.S.C. 154(b) by 269 days.

(21) Appl. No.: 13/582,456

(22) PCT Filed: Mar. 4, 2011

(86) PCT No.: PCT/KR2011/001485
§ 371 (c)(1), (2), (4) Date: Sep. 4, 2012

(87) PCT Pub. No.: WO2011/108873
PCT Pub. Date: Sep. 9, 2011

(65) Prior Publication Data
US 2012/0326876 A1     Dec. 27, 2012

(30) Foreign Application Priority Data

Mar. 4, 2010 (KR) ........................ 10-2010-0019379

(51) Int. Cl.
| | |
|---|---|
| A47B 13/00 | (2006.01) |
| A61G 7/10 | (2006.01) |
| A47C 21/00 | (2006.01) |
| F16M 13/00 | (2006.01) |
| F16D 1/00 | (2006.01) |
| A61F 5/37 | (2006.01) |
| A61B 6/04 | (2006.01) |
| A61G 7/012 | (2006.01) |

(52) U.S. Cl.
CPC ................ *A61G 7/1036* (2013.01); *A61B 6/04* (2013.01); *A61G 7/103* (2013.01); *A61G 7/012* (2013.01)

(58) Field of Classification Search
USPC ............ 340/573.4; 5/81.1 HS, 611, 606, 900, 5/601, 81, 1 HS; 180/11, 16, 1, 19.1; 248/125.8, 311.3, 391.1, 318
See application file for complete search history.

(56) References Cited

U.S. PATENT DOCUMENTS

| | | | | | |
|---|---|---|---|---|---|
| 3,709,372 | A | * | 1/1973 | Alexander | 211/74 |
| 3,815,164 | A | * | 6/1974 | Smith | 5/86.1 |
| 3,902,204 | A | * | 9/1975 | Lee | 5/86.1 |
| 3,917,076 | A | * | 11/1975 | Campbell | 414/642 |
| 4,016,612 | A | * | 4/1977 | Barile, Sr. | 5/200.1 |
| 4,019,772 | A | * | 4/1977 | Lee | 296/20 |
| 4,262,872 | A | * | 4/1981 | Kodet | 248/311.3 |
| 4,273,374 | A | * | 6/1981 | Portman | 296/19 |
| 4,277,218 | A | * | 7/1981 | Schweichler | 414/401 |
| 4,432,359 | A | * | 2/1984 | James | 5/87.1 |
| 4,489,454 | A | * | 12/1984 | Thompson | 5/503.1 |
| 4,658,450 | A | * | 4/1987 | Thompson | 5/607 |
| 4,720,881 | A | * | 1/1988 | Meyers | 5/640 |

(Continued)

Primary Examiner — Fekadeselassie Girma
(74) Attorney, Agent, or Firm — Revolution IP, PLLC

(57) ABSTRACT

The present invention relates to a functional table for patient transportation, including: a patient supporter which supports a patient laid thereon and allows the patient to be horizontally slidably transported, with its both sides being changed in their angle with respect to a vertical axis of the patient; a support frame which is located in the central bottom of the patient supporter and allows the patient supporter to be vertically moved; a base frame which is connected to the bottom of the support frame and supports the whole of functional table; and at least three transporting wheels which are connected to the base frame and allow the functional table to be freely moved.

8 Claims, 8 Drawing Sheets

(56) References Cited

U.S. PATENT DOCUMENTS

| | | | |
|---|---|---|---|
| 4,768,241 A * | 9/1988 | Beney | 5/600 |
| 4,939,801 A * | 7/1990 | Schaal et al. | 5/607 |
| 5,014,968 A * | 5/1991 | Lammers et al. | 5/611 |
| 5,016,307 A * | 5/1991 | Rebar | 5/503.1 |
| 5,083,331 A * | 1/1992 | Schnelle et al. | 5/600 |
| 5,111,541 A * | 5/1992 | Wagner | 5/601 |
| 5,117,521 A * | 6/1992 | Foster et al. | 5/510 |
| 5,187,821 A * | 2/1993 | Nieminen et al. | 5/83.1 |
| 5,235,319 A * | 8/1993 | Hill et al. | 340/573.4 |
| 5,285,539 A * | 2/1994 | Anderson et al. | 4/564.1 |
| 5,319,817 A * | 6/1994 | Hay et al. | 5/611 |
| 5,407,163 A * | 4/1995 | Kramer et al. | 248/291.1 |
| 5,461,740 A * | 10/1995 | Pearson | 5/611 |
| 5,475,884 A * | 12/1995 | Kirmse et al. | 5/601 |
| 5,487,195 A * | 1/1996 | Ray | 5/83.1 |
| 5,570,483 A * | 11/1996 | Williamson | 5/83.1 |
| 5,588,166 A * | 12/1996 | Burnett | 5/503.1 |
| 5,611,638 A * | 3/1997 | Dorr et al. | 403/327 |
| 5,651,150 A * | 7/1997 | Kanitzer et al. | 5/600 |
| 5,687,942 A * | 11/1997 | Johnson | 248/223.41 |
| 5,699,988 A * | 12/1997 | Boettger et al. | 248/122.1 |
| 5,844,488 A * | 12/1998 | Musick | 340/573.4 |
| 5,934,282 A * | 8/1999 | Young et al. | 128/870 |
| 5,987,670 A * | 11/1999 | Sims et al. | 5/600 |
| 6,073,285 A * | 6/2000 | Ambach et al. | 5/600 |
| 6,098,216 A * | 8/2000 | Williamson et al. | 5/86.1 |
| 6,101,644 A * | 8/2000 | Gagneur et al. | 5/81.1 R |
| 6,178,575 B1 * | 1/2001 | Harada | 5/600 |
| 6,374,438 B1 * | 4/2002 | Fox et al. | 5/600 |
| 6,375,133 B1 * | 4/2002 | Morrow | 248/125.8 |
| 6,421,853 B1 * | 7/2002 | Pecorelli et al. | 5/606 |
| 6,499,163 B1 * | 12/2002 | Stensby | 5/618 |
| 6,546,577 B1 * | 4/2003 | Chinn | 5/600 |
| 6,619,599 B2 * | 9/2003 | Elliott et al. | 248/125.8 |
| 6,640,364 B1 * | 11/2003 | Josephson et al. | 5/601 |
| 6,782,571 B1 * | 8/2004 | Josephson et al. | 5/601 |
| 6,854,140 B2 * | 2/2005 | Bartels et al. | 5/601 |
| 7,490,377 B2 * | 2/2009 | Ahlman | 5/81.1 R |
| 7,784,121 B2 * | 8/2010 | Ahlman | 5/81.1 R |
| 7,975,329 B2 * | 7/2011 | Patterson | 5/81.1 C |
| 8,046,851 B2 * | 11/2011 | Ahlman | 5/81.1 R |
| 8,096,004 B2 * | 1/2012 | Patterson | 5/81.1 HS |
| 8,214,944 B2 * | 7/2012 | Patterson | 5/81.1 C |
| 8,356,368 B2 * | 1/2013 | Patterson | 5/81.1 C |
| 8,381,335 B2 * | 2/2013 | Ahlman | 5/503.1 |
| 8,442,738 B2 * | 5/2013 | Patmore | 701/93 |
| 8,516,637 B2 * | 8/2013 | Karwal et al. | 5/608 |
| 2001/0044957 A1 * | 11/2001 | Hodgetts | 5/81.1 R |
| 2002/0042952 A1 * | 4/2002 | Smeed | 5/503.1 |
| 2002/0162926 A1 * | 11/2002 | Nguyen | 248/229.25 |
| 2002/0174485 A1 * | 11/2002 | Bartels | 5/601 |
| 2003/0101513 A1 * | 6/2003 | Wong | 5/601 |
| 2003/0213064 A1 * | 11/2003 | Johnson | 5/86.1 |
| 2004/0111800 A1 * | 6/2004 | Bartels et al. | 5/600 |
| 2005/0246833 A1 * | 11/2005 | Barth et al. | 5/81.1 R |
| 2007/0079438 A1 * | 4/2007 | Patterson | 5/81.1 C |
| 2007/0124858 A1 * | 6/2007 | Ahlman | 5/81.1 R |
| 2007/0283492 A1 * | 12/2007 | Gallant et al. | 5/86.1 |
| 2008/0022456 A1 * | 1/2008 | Patterson et al. | 5/81.1 C |
| 2008/0234555 A1 * | 9/2008 | Lafleche et al. | 600/300 |
| 2009/0083907 A1 * | 4/2009 | Ahlman | 5/620 |
| 2009/0241263 A1 * | 10/2009 | DeBraal et al. | 5/611 |
| 2010/0011501 A1 * | 1/2010 | Patterson | 5/81.1 C |
| 2011/0030142 A1 * | 2/2011 | Karwal et al. | 5/608 |
| 2011/0047704 A1 * | 3/2011 | DeBraal et al. | 5/611 |
| 2011/0067177 A1 * | 3/2011 | Patterson et al. | 5/81.1 C |
| 2011/0296609 A1 * | 12/2011 | Giap | 5/88.1 |
| 2012/0084914 A1 * | 4/2012 | Patterson et al. | 5/81.1 C |
| 2012/0186018 A1 * | 7/2012 | DeBraal et al. | 5/611 |
| 2012/0216345 A1 * | 8/2012 | Hand | 5/85.1 |
| 2013/0340167 A1 * | 12/2013 | Karwal et al. | 5/611 |

* cited by examiner

FUNCTIONAL TABLE FOR TRANSFERRING PATIENT

TECHNICAL FIELD

The present invention relates to a functional table for patient transportation, and more particularly, to a functional table for patient transportation which is capable of transporting patients with safety, ease and promptness without a risk of secondary damage to the patients.

BACKGROUND ART

As known in the art, there has been proposed a variety of apparatuses for transporting emergency patients, critical patients, bone-fracture patients and the like, who are impossible or nearly impossible to move for themselves, from one place to another.

A patient in a hospital may be often moved from his/her hospital bed to a medical examination table or an operating table and vice versa. Primary equipment may include a stretcher carried by an assistant and a patient transporting bed with wheels.

However, there is a problem in moving the patient from the hospital bed to the stretcher or the patient transporting bed. For example, although it is a simple task to move the patient in support of the assistant if the patient is cooperative or can move for himself, there may be a challengeable task to move the patient from the hospital bed to the stretcher or the patient transporting bed if the patient is unconscious or has a damage such as a bone-fracture or an injury, which may be worsened by movement.

For the purpose of overcoming the above problem, a patient transporting apparatus is disclosed in, for example, Korean Patent Application Publication No. 2003-0073921.

The disclosed patient transporting apparatus is for transporting a patient who is laid on a stretcher placed on a carrier body. However, this has a problem in that it requires two assistants who have to lift the stretcher from its both sides when the patient is transported from one bed to another, and the weight of the stretcher to support the patient is still the same. In addition, a secondary damage may occur if the assistants miss the stretcher.

Moreover, there is a further problem that a patient who cannot be moved at all has to receive help from at least another assistant in order to transport and safely lay the patient on another table.

DISCLOSURE OF INVENTION

Technical Problem

To overcome the above problems, it is an object of the present invention to provide a functional table for patient transportation which is capable of transporting patients to a variety of medical examination tables with safety, ease and promptness.

It is another object of the present invention to provide an apparatus which is capable of transporting emergency patients, critical patients, bone-fracture patients and the like, who are difficult or impossible to move for themselves, from one table to another without a risk of secondary damage to the patients.

Technical Solution

To achieve the above and other objects, according to a first aspect, the present invention provides a functional table for patient transportation, including: a patient supporter which supports a patient laid thereon and allows the patient to be horizontally slidably transported, with its both sides being changed in their angle with respect to a vertical axis of the patient; a support frame which is located in the central bottom of the patient supporter and allows the patient supporter to be vertically moved; a base frame which is connected to the bottom of the support frame and supports the whole of functional table; and at least three transporting wheels which are connected to the base frame and allow the functional table to be freely moved.

Preferably, a protective support bar for preventing the patient from being get out of the functional table is provided in both sides of the patient supporter. Preferably, the support bar includes a railing sensor to sense movement of the patient and generate an alarm if the patient is to get out of the functional table.

Preferably, the support frame is formed of a plurality of stages, the lowest one of which is fixed without vertical movement. Preferably, the support frame includes a cylinder connected to the base frame, and a hydraulic actuator which actuates the cylinder vertically by a hydraulic pressure (or a pneumatic pressure or an electric motor).

Preferably, the base frame is formed of a square frame and the transporting wheels are provided in side edges of the base frame. Preferably, one side of the patient supporter is formed of two stages, the upper one of which includes a guide rail and a nonmagnetic roller to allow the upper one to be horizontally slid. Preferably, the transporting wheels include an electricity-free driving controller.

Advantageous Effects

The present invention can provide a patient transportation functional table which is capable of transporting a patient to a variety of medical examination tables with ease, safety and promptness since the functional table can be vertically ascended/descended, its ones side can be horizontally moved, and its both sides can be rotated at a certain angle with respect to the vertical axis of the table, unlike conventional patient transportation apparatuses.

In addition, the present invention can provide a patient transportation functional table which is capable of transporting emergency patients, critical patients, bone-fracture patients and the like, who are difficult or impossible to move for themselves, from one table to another without a risk of secondary damage to the patients.

BEST MODE FOR CARRYING OUT THE INVENTION

Hereinafter, preferred embodiments of the present invention will be described in detail with reference to the accompanying drawings.

Figure 1:
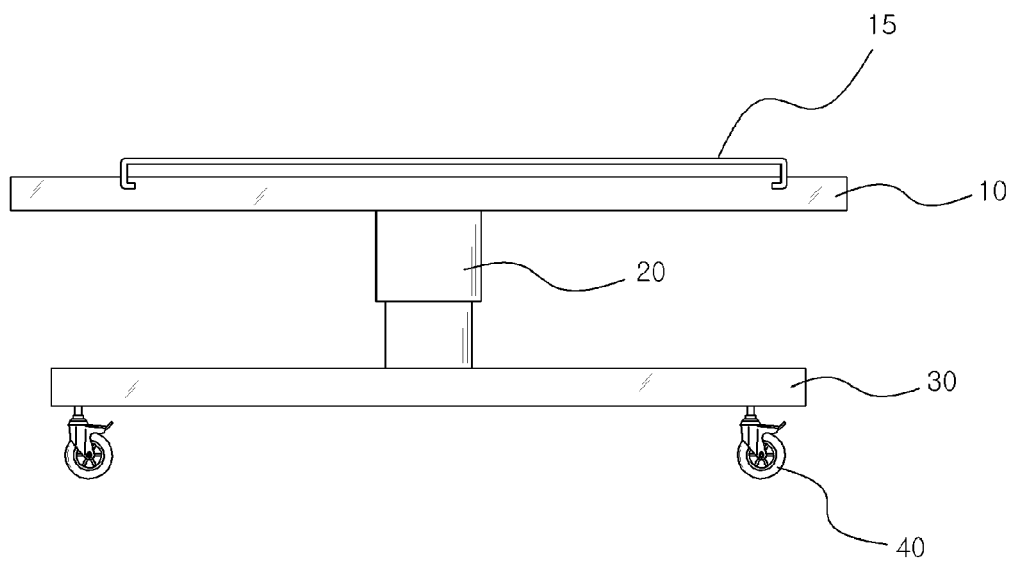
FIG. 1 is a view illustrating a side of a functional table for patient transportation according to the present invention.

FIG. 1 is a view illustrating a side of a functional table for patient transportation according to an embodiment of the present invention. As shown in FIG. 1, a functional table of the present invention includes a patient supporter to support a patient 100 (see FIG. 4), a vertically-movable support frame 20 to support the patient supporter 10, a base frame 30 which is connected to the bottom of the support frame 20 and supports the whole of functional table, and transporting wheels 40 which are connected to the bottom of the base frame 30 to allow the functional table to be freely moved in every direction.

In this manner, the functional table of the present invention is so configured that the patient supporter 10 on which the patient 10 is laid can be adjusted in its height by the vertically-movable support frame 20 connected to the central bottom of the patient supporter 10 as needed, and the functional table can be moved in every direction by the transporting wheels 40 connected to edges of the base frame 30 connected to the bottom of the support frame 20 to support the functional table.

Such a configuration allows the patient 100 to be transported to a medical examination table 200 (see FIG. 4) with more ease, convenience and safety without immoderate movement.

Figure 2:
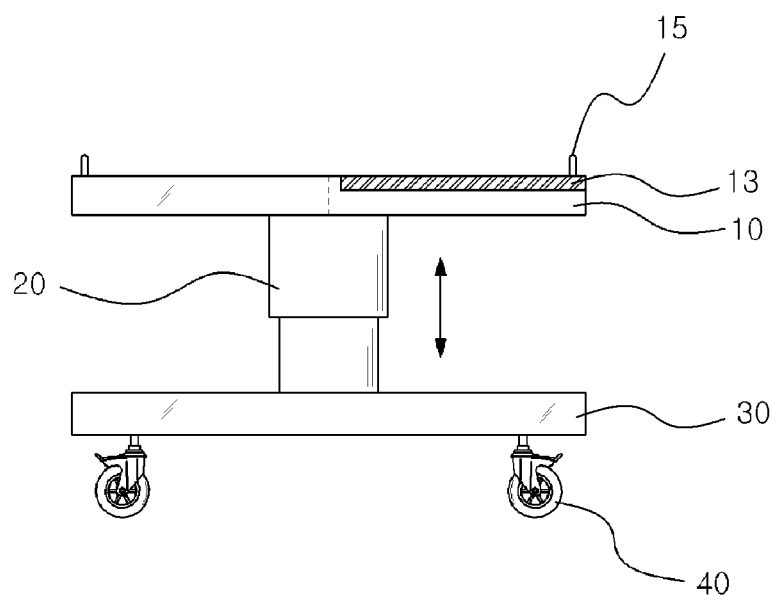
FIG. 2 is a view illustrating a front of the functional table for patient transportation according to the present invention.

FIG. 2 is a view illustrating a front of the functional table for patient transportation according to an embodiment of the present invention. As shown in FIG. 2, the functional table has a structure in which the patient supporter 10 has two sides which are folded at a certain angle in a vertical direction in which the patient 100 is laid, with one of the two sides formed of two or more stages and with an upper portion of the one of the two sides being slidable in the vertical direction.

Such a structure allows for safe transportation of the patient 100 whose movement has to be minimized to prevent a backbone damage and so on when the patient 100 is transported to/out of the table.

This structure is differentiated from conventional simple sliding transportation structures in that the table can be vertically moved, with its both sides being inclined at a certain angle with respect to the patient 100 and with multi-staged one of the sides being slid in the vertical.

Figure 3:
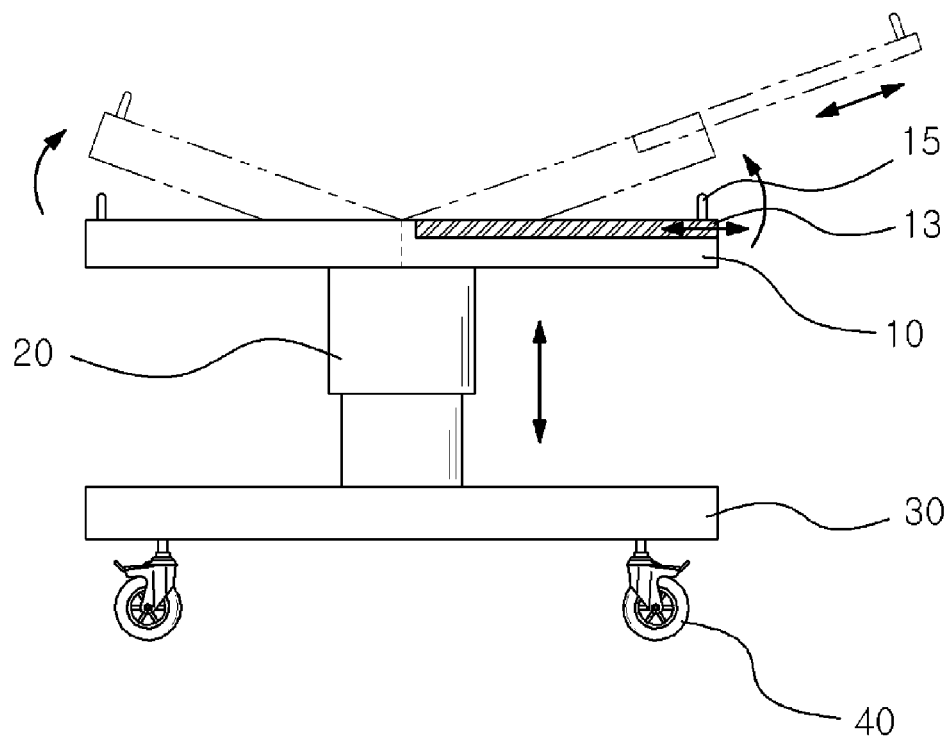
FIG. 3 is a front view showing an operation of the functional table for patient transportation according to the present invention.

FIG. 3 is a front view showing an operation of the functional table for patient transportation according to the present invention. In more detail, FIG. 3 shows a change in an angle of the functional table in the vertical direction and a sliding structure. As shown in FIG. 3, the functional table has a structure in which the patient supporter 10 can be vertically moved by driving of the support frame 20 located in the lower center of the patient supporter 10 and can be inclined by changing its both sides by a certain angle, and an upper sliding supporter 13 can be slid by virtue of a two-staged structure of one of the sides.

Such a structure aims at safe and easy transportation of the patient 100 from the functional table to medical examination equipment such as CT, MRI and so on.

In other words, a traditional patient transportation table has a problem that a patient has to be moved by help of others from the patient transportation table to a medical examination equipment table since the former has a height different from that of the latter and a further safety problem that this process forces immoderate force or movement to be taken by the patient whose action or movement has to be minimized.

To overcome these problems, the patient transportation functional table of the present invention includes the support frame 20 to adjust the height of the patient supporter 10 to the height of the medical examination equipment table with ease and has a structure in which the sliding supporter 13 on which the patient 100 is laid can be slid from the patent transportation functional table to the medical examination equipment table for safe transportation of the patient 100 with minimized movement of the patient 100.

In addition, a support bar to prevent the patient 100 from being get out of the functional table is preferably provided in a side of the patient supporter 10. The support bar serves as a protection support as well as a grip grasped by the patient 100 who intends to be relaxed. This protective support bar is provided in both sides of the functional table and may include a railing sensor used to prevent the patient 100 from being get out of the table unconsciously. This railing sensor can sense movement of the patient 100 and generate an alarm or the like if the patient 100 is to get out of the functional table, thereby providing a safer functional table.

In addition, one side of the patient supporter 10 is formed of a multi-staged sliding driver which has guide rails formed in its both sides. In addition, preferably, a nonmagnetic roller connected to the guide rails is rolled in a horizontal direction. Alternatively, a multi-staged supporter may be employed as long as it can be slid.

In addition, preferably, the support frame includes a cylinder connected to the base frame 30 and a hydraulic actuator to actuate the cylinder vertically using a hydraulic pressure. As one example, although not shown, the hydraulic actuator may include an electric motor, a hydraulic pump driven by the electric motor for oil pumping, an oil tank connected to the hydraulic pump by a first connecting pipe for oil storage, and a second connecting pipe to connect the hydraulic pump and the cylinder so that oil can be fed from the hydraulic pump to the cylinder. Alternatively, although not shown, the hydraulic actuator may include an electric motor and a screw bar which is rotatably connected to the shaft of the electric motor and has threads screwed to the bottom of the support frame.

The patient transportation functional table of the present invention can be freely moved in every direction by the transporting wheels 40 provided in four bottom edges of the base frame 30. The transporting wheels 40 preferably include an electricity-free driving controller. This is because continued rotation and movement of the wheels 40 may generate static electricity due to friction with the ground, which may be delivered to the patient 100 or other medical equipment, thereby putting them in danger. Accordingly, it is advantageous to include a device which is able to prevent the static electricity from being introduced into the patient 100 and selectively automatically drive the wheels 40 and a driving controller to control the device.

A process of transporting the patient 100 from the patient transportation functional table to the medical examination equipment table and vice versa and effects thereof will be now described with reference to the relevant figures.

Figure 4:
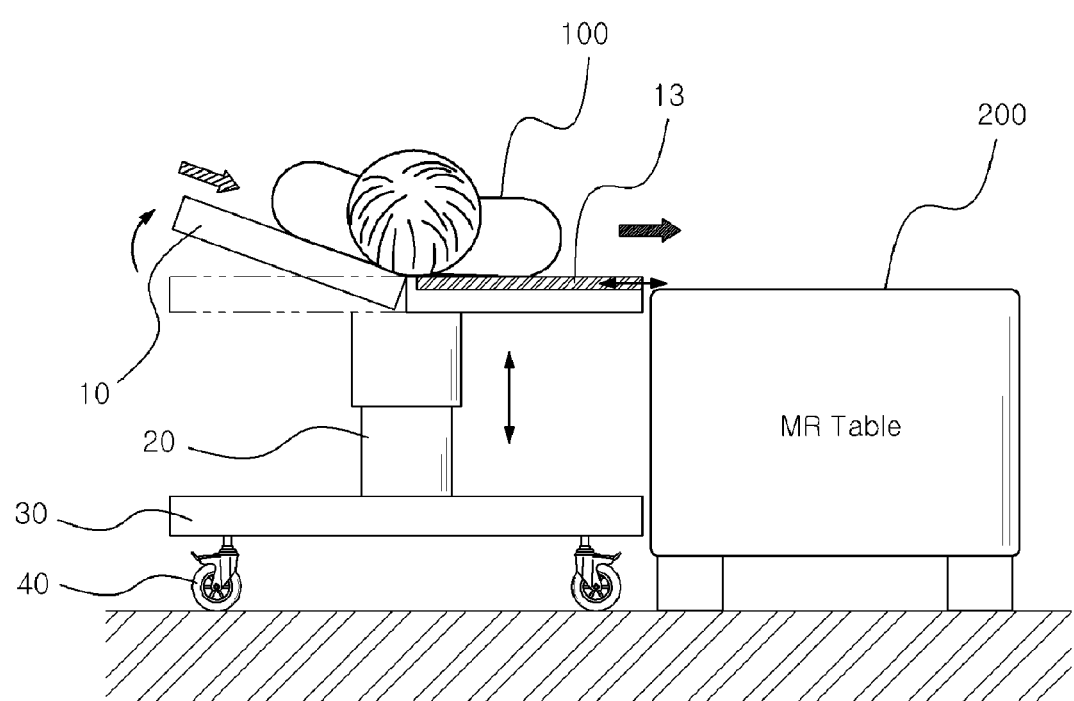
FIG. 4 is a view showing a process of approaching a patient to an examination equipment table before transporting the patient from the functional table for patient transportation according to the present invention to the examination equipment table.
Figure 5:
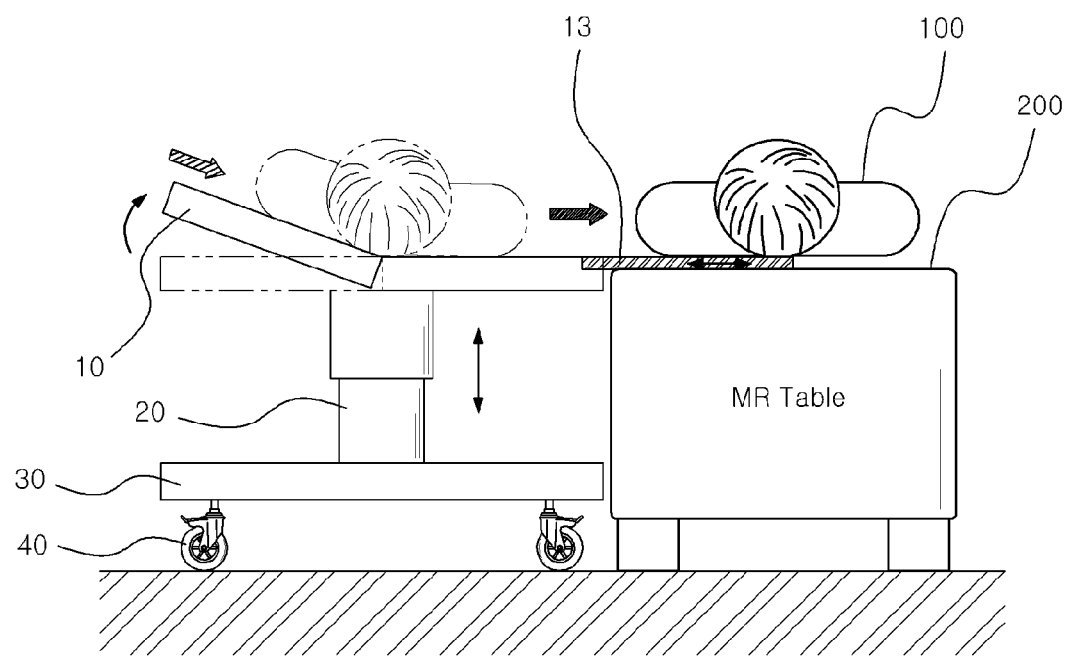
FIG. 5 is a view showing an operation of transporting the patient to the examination equipment table through sliding of the functional table for patient transportation according to the present invention.
Figure 6:
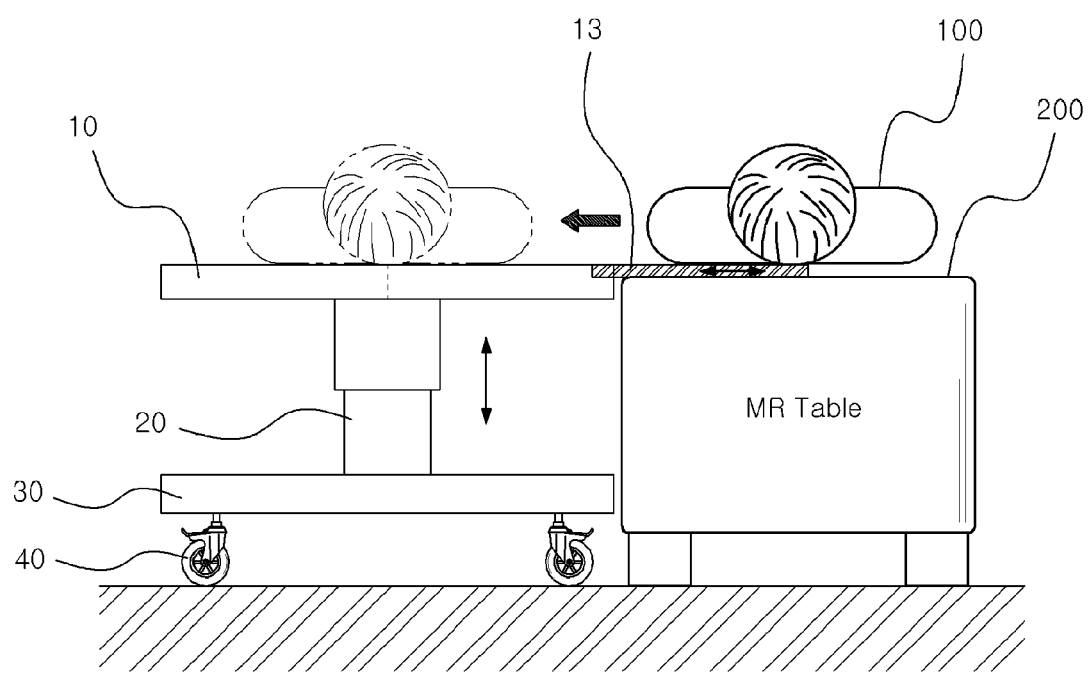
FIG. 6 is a view showing an operation of approaching the examination equipment table to the patient through the sliding before transporting the patient to the functional table.
Figure 7:
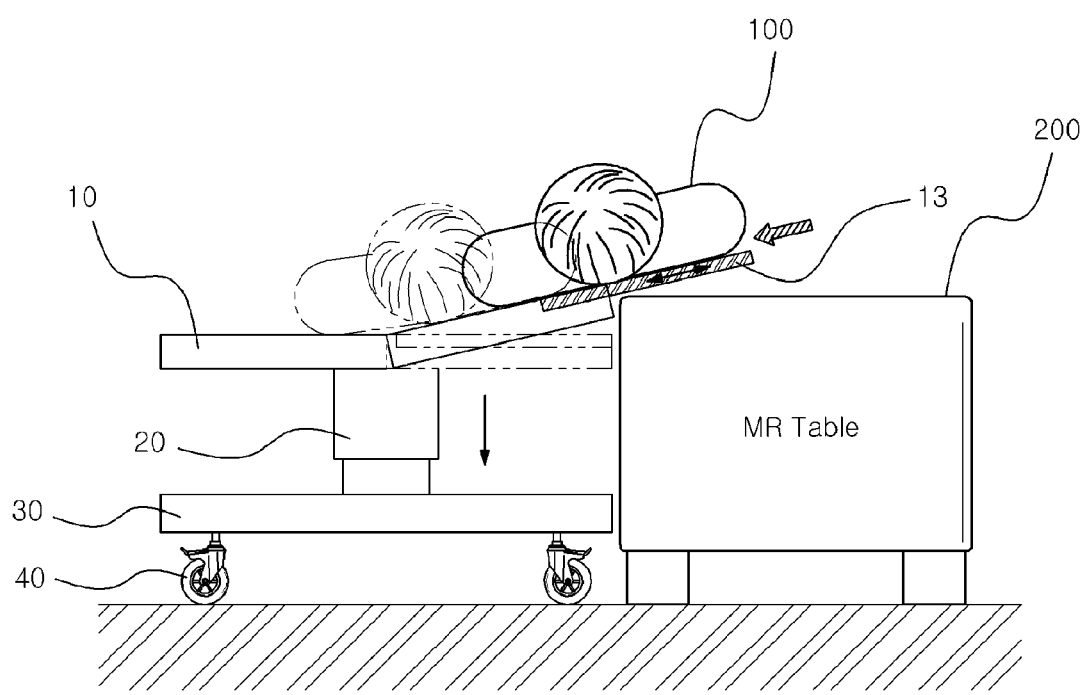
FIG. 7 is a view showing an operation of an apparatus for transporting the patient lying on a sliding supporter to the functional table.

FIGS. 4 and 5 are views showing a process of transporting the patient 100 from the functional table to the medical examination equipment table. As shown in FIG. 4, the functional table on which the patient 100 is laid approaches the examination table and the support frame is driven to adjust the height of the functional table to the height of the examination table. Thereafter, one opposing side of the patient supporter 10 adjacent to the examination table is rotated and ascended such that it is inclined at a certain angle.

Then, the patient 100 can be slidably moved by the inclination according to the gravity in the opposite direction and, accordingly, can be horizontally naturally moved toward the examination table without significant movement. In this manner, the patient 100 can be naturally and safely moved by the functional table which is able to be rotated at a certain angle around the vertical axis of the patient 100.

FIG. 5 is a view showing an operation of transporting the patient 100 from the functional table to the examination table. As shown in FIG. 5, when the patient 100 is horizontally moved to the examination table by the table vertical axial rotation, a portion of the patient 100 who lies on the functional table is leaned toward the sliding supporter 13. As one side of the patient supporter 10 on which the patient 100 lies has a two-staged sliding structure, the patient 100 can be transported to the examination table with safety and convenience by sliding and moving the upper sliding supporter 13 to the examination table.

In this manner, according to the present invention, the patient 100 can be transported to the examination table only by actuation of the functional table with ease, safety and promptness without help of others.

FIGS. 6 to 9 are views showing a process of transporting the patient 100 from the examination table to the patient transportation functional table. As shown in FIG. 6, the patient 100 is again moved to the examination table after the patient 100 is examined in the examination table. With the patient 100 lying on the examination table, the functional table is moved to the examination table and is adjusted in height to the examination table by driving the support frame 20.

At the same height of the examination table and the functional table, the multi-staged sliding supporter 13 is slidably moved to support the patient 100 at one side of the functional table adjacent to the examination table.

Then, referring to FIG. 7, in order to again move the patient 100 to the functional table, instead of horizontally moving the sliding supporter at the same height, when the support frame 20 of the functional table is descended to lower the functional table, one side of the patient supporter 10 supporting the sliding supporter is leaned at a certain angle so that the sliding supporter 13 can be horizontally naturally moved to the functional table by the gravity, as shown in FIG. 7.

Figure 8:
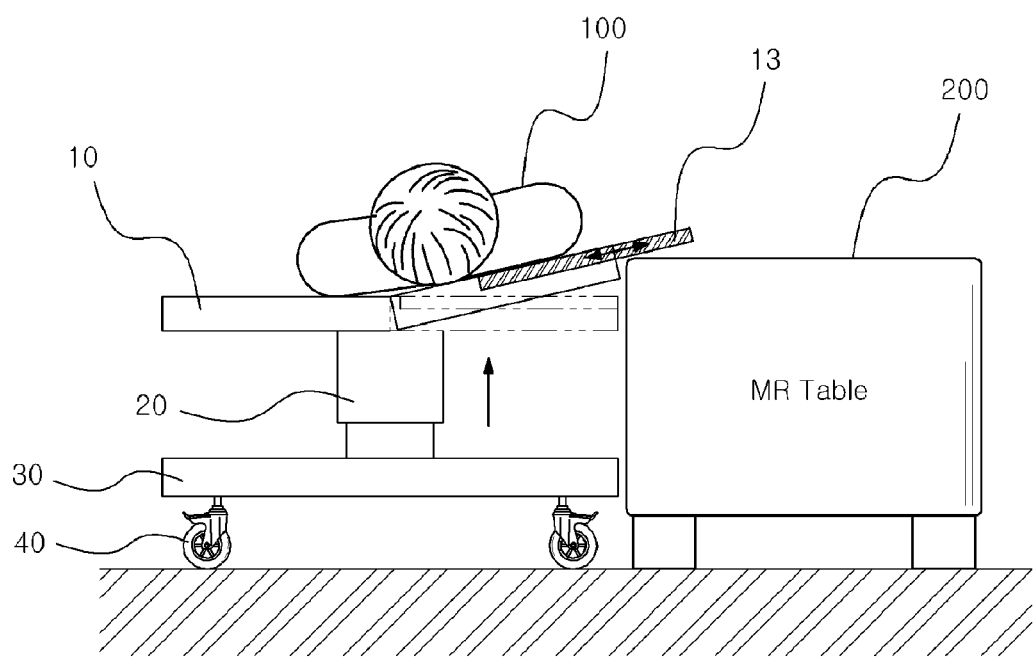
FIG. 8 is a view showing an operation of an apparatus for placing the patient on the central portion of the functional table with safety.

Once the support frame of the functional table is descended to make a tilt angle and the patient 100 is slidably moved with the sliding supporter 13 by the tilt, the patient 100 can be placed in the central portion of the functional table with safety and promptness when the support frame 20 is again ascended, as shown in FIG. 8.

Figure 9:
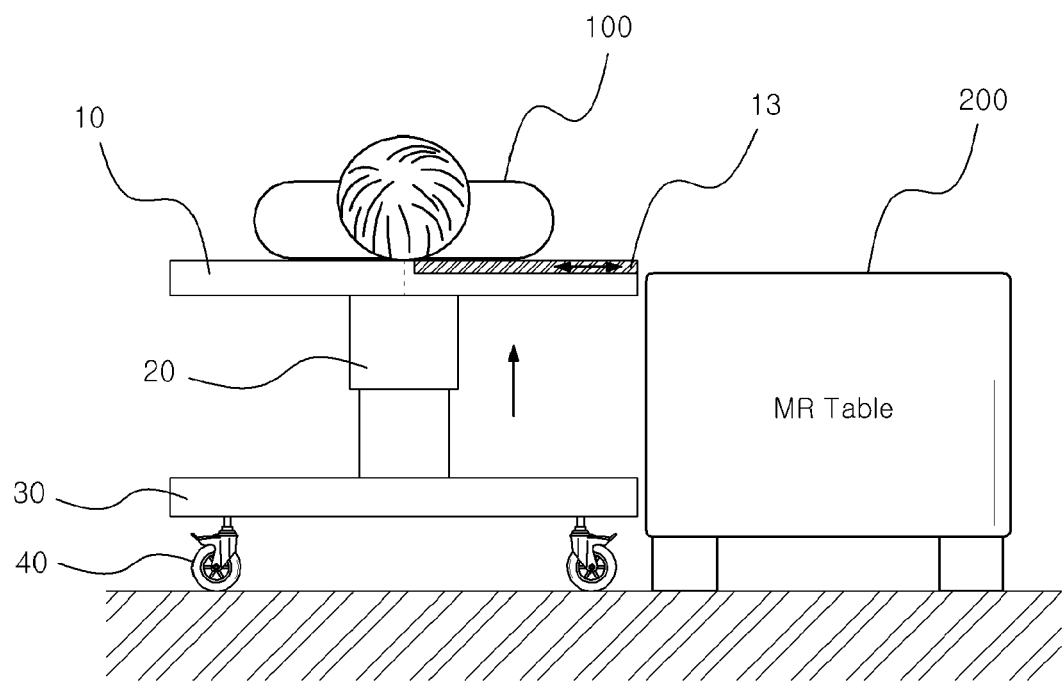
FIG. 9 is a view showing an operation of finally placing the patient on the functional table with safety and returning a sliding supporter to its original position.

Then, finally, as shown in FIG. 9, by moving the sliding supporter 13 to its original position and ascending and stopping the support frame to its original position, the patient 100 can be transported from the examination table to the patient transportation functional table with ease, safety and promptness.

Although a few exemplary embodiments have been shown and described, it will be appreciated by those skilled in the art that adaptations and changes may be made in these exemplary embodiments without departing from the spirit and scope of the invention, the scope of which is defined in the appended claims and their equivalents.

INDUSTRIAL APPLICABILITY

The present invention provides a patient transportation functional table which is capable of transporting a patient to a variety of medical examination tables with ease, safety and promptness since the functional table can be vertically ascended/descended, its ones side can be horizontally moved, and its both sides can be rotated at a certain angle with respect to the vertical axis of the table, unlike conventional patient transportation apparatuses.

The patient transportation functional table can be preferentially applied to rescue and emergency for emergency patients, critical patients, bone-fracture patients and the like, who are difficult or impossible to move for themselves, and further rehabilitation and medical treatment for the aged and disabled.

The invention claimed is:

1. A functional table for patient transportation, comprising:
a patient supporter, having a longitudinal direction and a lateral direction, being folded in half in the longitudinal direction, and configured to support a patient laid thereon and to allow the patient to be slidably transported to an examination table according to a tilt angle with respect to the folded portion in a central portion of the patient supporter;
a sliding supporter configured, at one side of the patient supporter, to be slidably extended to the examination table in which the patient is transported between the functional table and the examination table, wherein
when moving the patient from the patient supporter to the examination table, a portion of the patient supporter is folded upward position to slidably move the patient toward the sliding supporter,
when moving the patient from the examination table to the patient supporter, one side of the patient supporter is folded at a certain angle so that the patient can be moved to the patient supporter by gravity;
a support frame, located in the central bottom of the patient supporter, configured to be adjusted in an upward and downward directions to make a horizontal level between the functional table and the examination table;
a base frame being connected to the bottom of the support frame and configured to support the functional table; and
at least three transporting wheels configured to be connected to the base frame and to allow the functional table to be freely moved.

2. The functional table of claim 1, wherein a protective support bar is configured to prevent the patient from being get out of the functional table, and is provided in both sides of the patient supporter.

3. The functional table of claim 2, wherein the support bar includes a railing sensor to sense movement of the patient and to generate an alarm if the patient is to get out of the functional table.

4. The functional table of claim 1, wherein the support frame is formed of a plurality of stages, the lowest one of which is fixed without vertical movement.

5. The functional table of claim 3, wherein the support frame includes a cylinder connected to the base frame, and a hydraulic actuator configured to actuate the cylinder vertically by a hydraulic pressure.

6. The functional table of claim 1, wherein the base frame is formed of a square frame and the transporting wheels are provided in side edges of the base frame.

7. The functional table of claim 1, wherein the one side of the patient supporter is formed of two stages, the upper one of which includes a guide rail and a nonmagnetic roller to allow the upper one to be horizontally slid.

8. The functional table of claim 1, wherein the transporting wheels include an electricity-free driving controller.

* * * * *